United States Patent
Gao et al.

(10) Patent No.: US 6,689,744 B2
(45) Date of Patent: Feb. 10, 2004

(54) NOTCH RECEPTOR AGONISTS AND USES

(75) Inventors: Wei-Qiang Gao, Palo Alto, CA (US); Hartmut Koeppen, Berkeley, CA (US); Sarajane Ross, San Francisco, CA (US); Jianyong Shou, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/954,736

(22) Filed: Sep. 17, 2001

(65) Prior Publication Data

US 2003/0082651 A1 May 1, 2003

Related U.S. Application Data

(60) Provisional application No. 60/234,674, filed on Sep. 22, 2000.

(51) Int. Cl.[7] .................. A61K 38/00; A61K 39/395; C07K 14/00; C07K 16/00
(52) U.S. Cl. .................. 514/2; 424/138.1; 424/139.1; 424/145.1; 424/155.1; 424/158.1; 530/350; 530/388.1; 530/389.1
(58) Field of Search ................ 514/2; 530/350, 530/388.1, 389.1; 424/138.1, 139.1, 145.1, 155.1, 158.1

(56) References Cited

U.S. PATENT DOCUMENTS

| | | |
|---|---|---|
| 4,933,294 A | 6/1990 | Waterfield et al. |
| 5,401,638 A | 3/1995 | Carney et al. |

FOREIGN PATENT DOCUMENTS

| | | |
|---|---|---|
| WO | WO 91/05264 | 4/1991 |
| WO | WO 98/20142 | 5/1998 |
| WO | WO 99/04746 | 2/1999 |

OTHER PUBLICATIONS

Curti, Crit. Rev. in Oncology/Hematology, 1993, vol. 14, pp. 29–39.*
Morris et al. Cancer, 2000, vol. 89(6), pp. 1329–1348.*
Gura, Science, 1997, vol. 278, pp. 1041–1042.*
Weinstein et al. Curr. Pharm. Des., 2000, 6(4), pp. 473–483.*
Artavanis–Tsakonas et al., "Notch Signaling." *Science*, 268:225–232 (Apr. 14, 1995).
Gingrich et al., "Androgen–Independent Prostate Cancer Progression in the TRAMP Model." *Cancer Research* 57:4687–4691 (Nov. 1, 1997).
Gingrich et al., "Metastatic Prostate Cancer in a Transgenic Mouse." *Cancer Research*. 56:4096–4102 (Sep. 15, 1996).
Gingrich et al., "Pathologic Progression of Autochthonous Prostate Cancer in the TRAMP Model." *Prostate Cancer and Prostatic Diseases*. 2:70–75 (1995).
Greenberg et al., "Prostate Cancer in a Transgenic Mouse." *Proc. Natl. Acad. Sci. USA* 92:3439–3443 (1995).
Hayward et al., "Epithelial Development in the Rat Ventral Prostate, Anterior Prostate and Seminal Vesicle." *Acta Anatomica* 155:81–93 (1996).
Honjo, Tasuku., "The Shortest Path From the Surface to the Nucleus: RBP–Jκ/Su (H) Transcription Factor." *Genes to Cells*. 1:1–9 (1996).
Lewis et al., "Distinct Expression Patterns of Notch Family Receptors and Ligands During Development of the Mammalian Inner Ear." *Mechanisms of Develop*. 78:159–163 (1998).
Nofziger et al., "Notch Signaling Imposes Two Distinct Blocks in the Differentiation of C2C12 Myoblasts." *Development*. 126 (1689–1702) (1999).
Nye et al., "An Activated Notch Suppresses Neurogenesis and Myogenesis But Not Gliogenesis in Mammalian Cells," *Development* 120:2421–2430 (1994).
Sias et al., "ELISA for Quantitcation of the Extracellular Domain of p185HER2 in Biological Fluids." *Journal of Immunological Methods* 132 (1):73–80 (1990).
Zheng et al., "Heregulin Enhances Regenerative Proliferation in Postnatal Rat Utricular Sensory Epithelium After Ototoxic Damage. " *J. Neurocytology* 28:901–912 (1999).
Lindsell et al., "Jagged: A Mammalian Ligand That Activates Notch1." *Cell*. 80:909–917 (Mar. 1995).
Luo et al., "Isolation and Functional Analysis of a cDNA for Human Jagged2, a Gene Encoding a Ligand for the Notch1 Receptor." *Mol. Cell. Bio*. 17(10):6057–6067 (Oct. 1997).
Shou et al., "Dynamics of Notch Expression During Murine Prostate Development and Tumorigenesis." *Cancer Research* . 61:7291–7297 (Oct. 2001).
Zlobin et al., "Toward The Rational Design of Cell Fate Modifiers: Notch Signaling as a Target for Novel Biopharmaceuticals." *Current Pharm. Biotech*. 1:83–106 (2000).

* cited by examiner

Primary Examiner—Yvonne Eyler
Assistant Examiner—Janet L. Andres
(74) Attorney, Agent, or Firm—David A. Carpenter

(57) ABSTRACT

The present invention is directed to methods of alleviating prostate disorders by activation of the Notch1 receptor. Also provided herein are methods for detecting and diagnosing prostate disorders, wherein the specific disorder is prostate cancer.

9 Claims, 5 Drawing Sheets

(3 of 5 Drawing Sheet(s) Filed in Color)

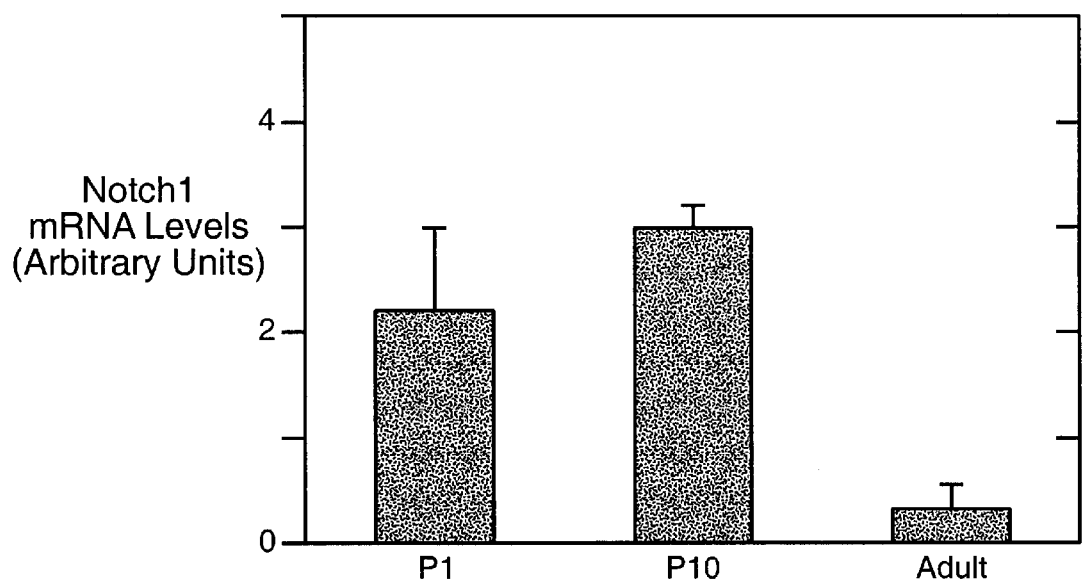
FIG._1A
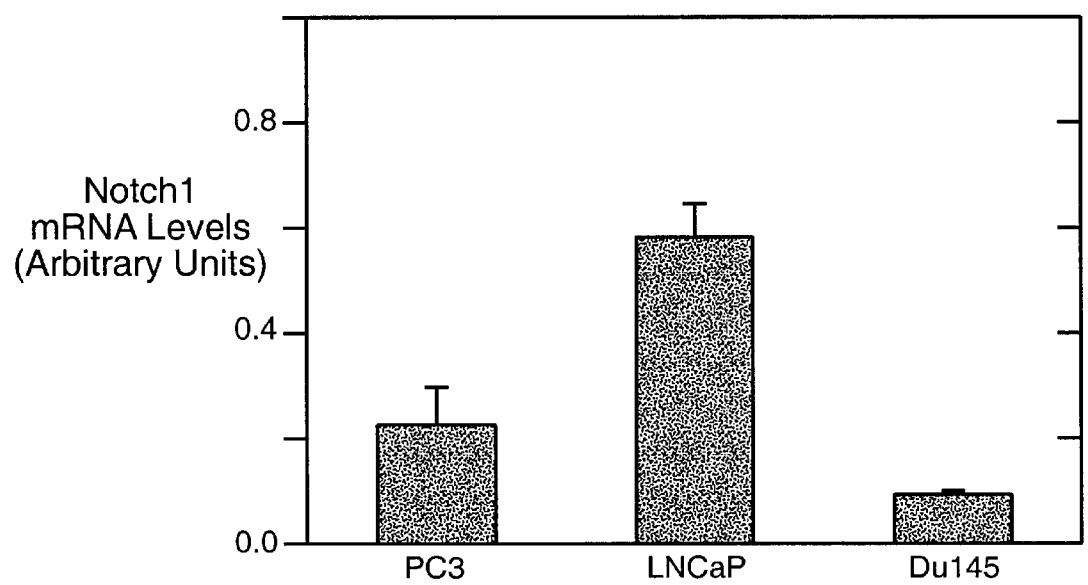
FIG._3

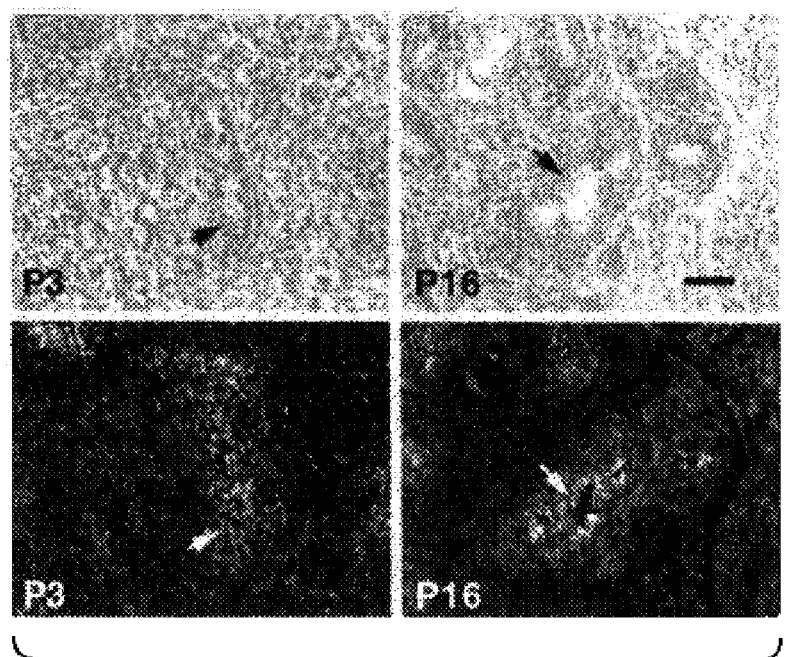
FIG._1B
FIG._2A  FIG._2B  FIG._2C
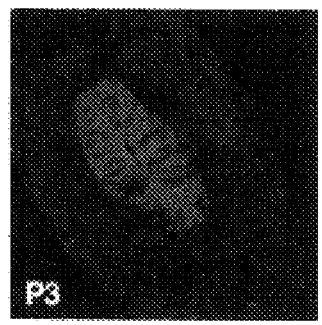 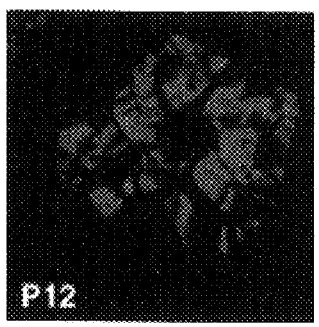 
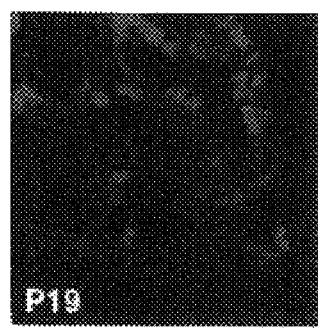 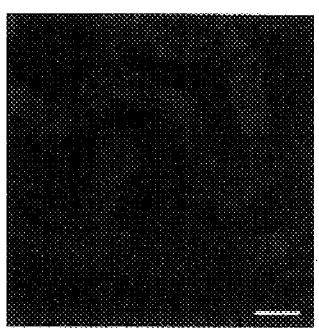 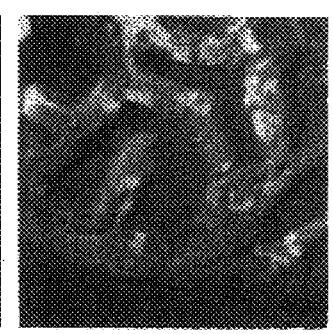
FIG._2D-1  FIG._2D-2  FIG._2D-3

FIG._4A
FIG._4B
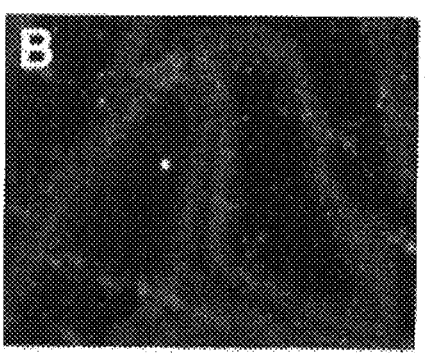
FIG._4C
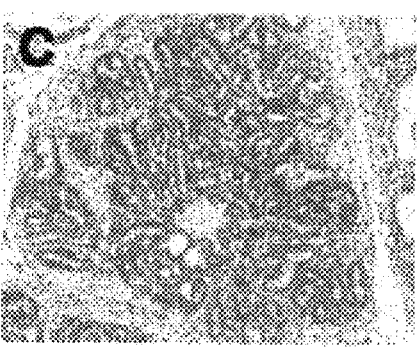
FIG._4D
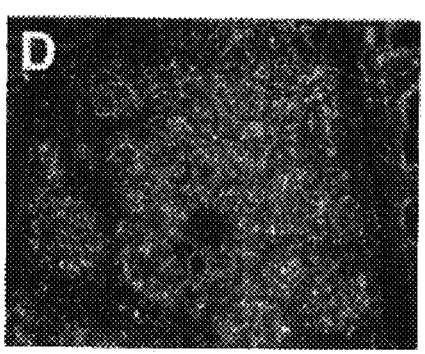
FIG._4E
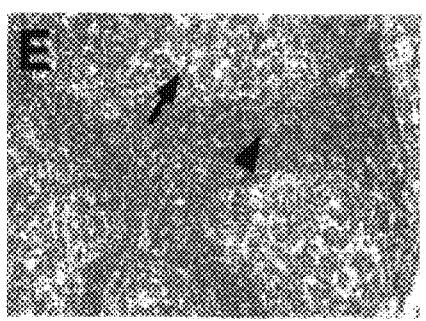
FIG._4F
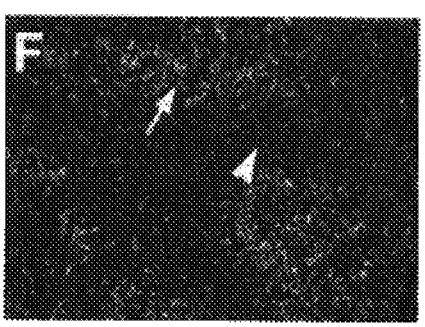
FIG._4G
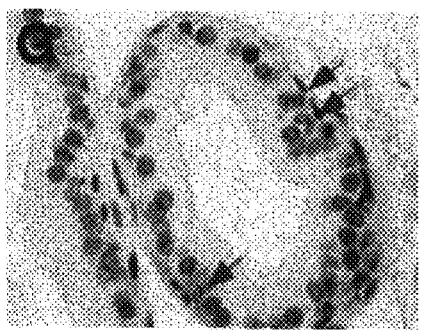
FIG._4H
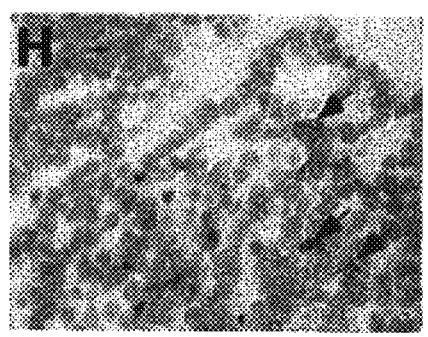

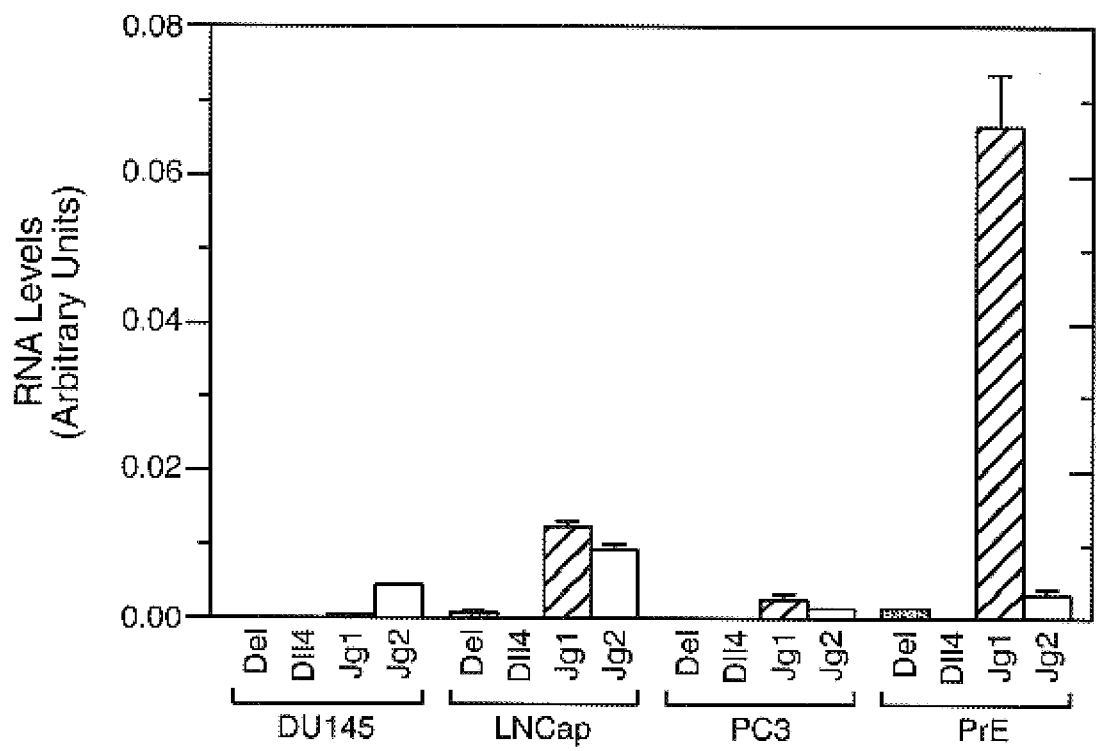
*FIG._5A*
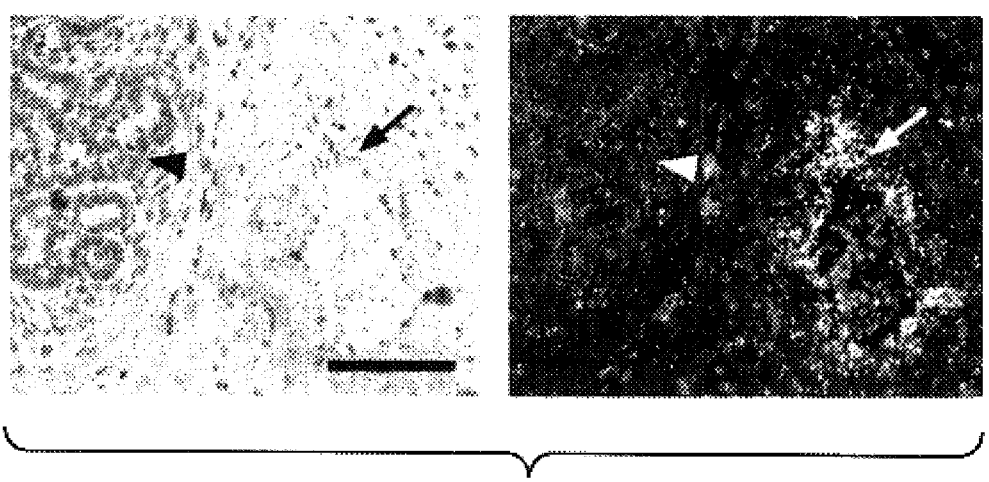
*FIG._5B*

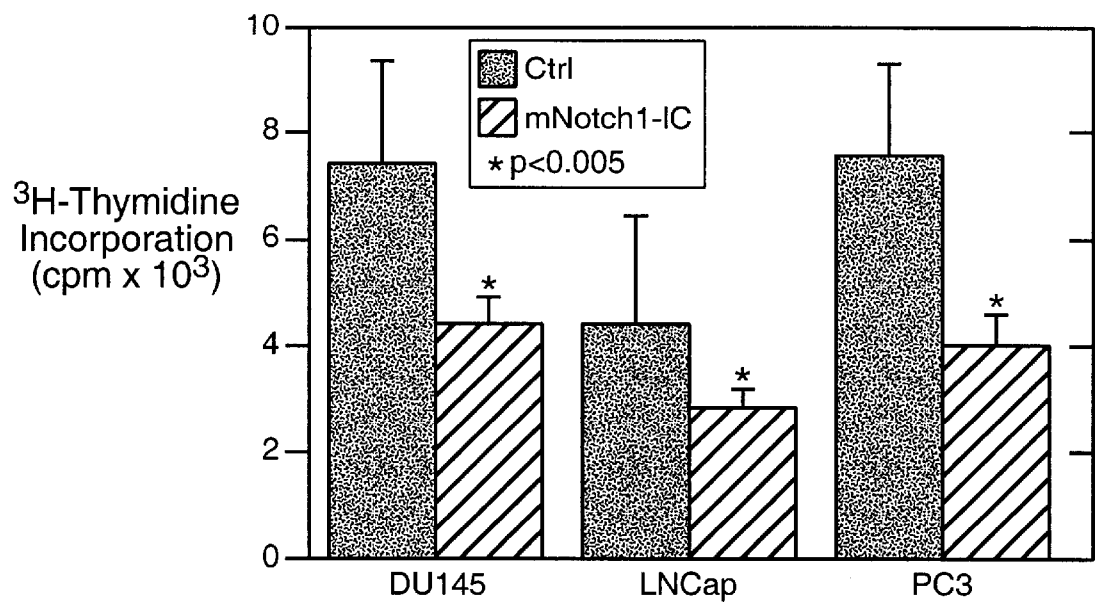
FIG._6A
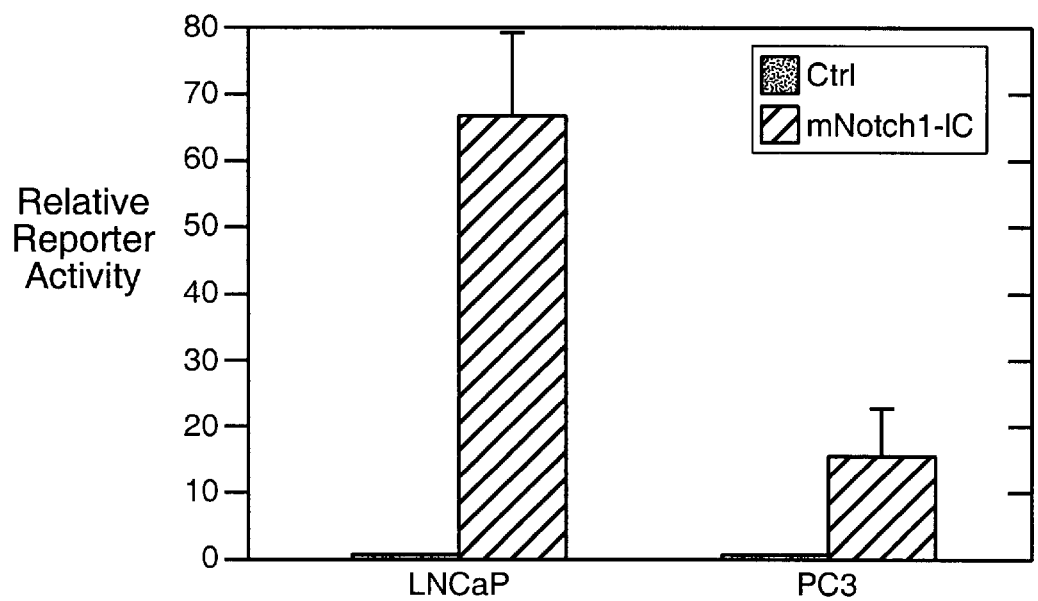
FIG._6B

SEQUENCE LISTING

<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 1
ggagaggctg ccaaggtttt                                               20

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 2
gcaaattggc cgtcagga                                                 18

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 3
cggcttccaa gtggtgccgg                                               20

<210> SEQ ID NO 4
<211> LENGTH: 16
<212> TYPE: DNA
<213> ORGANISM: Artificial Sequence
<220> FEATURE:
<223> OTHER INFORMATION: Synthetic Oligonucleotide Probe

<400> SEQUENCE: 4
cagtgtgggc gggtcc                                                   16

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 5
gttgtattgg ttcggcacca t                                             21

<210> SEQ ID NO 6
<211> LENGTH: 19
<212> TYPE: DNA
<213> ORGANISM: Homo Sapien
<220> FEATURE:
<221> NAME/KEY: Artificial Sequence
<222> LOCATION: full
<223> OTHER INFORMATION: Synthetic Oligonucleotide Probe

<400> SEQUENCE: 6
ccgctctgca gccgggaca                                                19

```
<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 7
ctcctccacc tttgacgctg                                               20

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 8
cataccagga aatgagcttg acaa                                          24

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 9
ctggcattgc cctcaacgac cac                                           23

<210> SEQ ID NO 10
<211> LENGTH: 17
<212> TYPE: DNA
<213> ORGANISM: Artificial Sequence
<220> FEATURE:
<223> OTHER INFORMATION: Synthetic Oligonucleotide Probe

<400> SEQUENCE: 10
caaccgcatc gtgctgc                                                  17

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 11
cgcctccaca agcaacgtat                                               20

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 12
cctcggccag gcgaaactga aa                                            22

<210> SEQ ID NO 13
<211> LENGTH: 23
<212> TYPE: DNA
<213> ORGANISM: Artificial Sequence
<220> FEATURE:
<223> OTHER INFORMATION: Synthetic Oligonucleotide Probe
```

-continued

```
<400> SEQUENCE: 13
cgctgtatga aaggagagag caa                                              23

<210> SEQ ID NO 14
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 14
ccgagtgagg aataaaagga agatt                                            25

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 15
tgcacaacct ctggtaacaa acgcga                                           26

<210> SEQ ID NO 16
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 16
tgtgtgacga acactactac ggag                                             24

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 17
gtgaagtggc cgaaggca                                                    18

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 18
ttctgccgtc cccgggacg                                                   19

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 19
ctggagctca gcgagtgtga c                                                21

<210> SEQ ID NO 20
<211> LENGTH: 20
```

```
<212> TYPE: DNA
<213> ORGANISM: Artificial Sequence
<220> FEATURE:
<223> OTHER INFORMATION: Synthetic Oligonucleotide Probe

<400> SEQUENCE: 20
gccatcctcc tggtccttac                                                    20

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 21
acccctgtcg caatggaggc ag                                                 22
```

NOTCH RECEPTOR AGONISTS AND USES

This application claims the benefit of provisional application No. 60/234,674 filed on Sep. 22, 2000.

FIELD OF THE INVENTION

The present invention relates to the activation of Notch receptor signaling to decrease cancer cell proliferation.

BACKGROUND OF THE INVENTION

Notch encodes a large protein with a single transmembrane domain, a large extracellular domain that has many tandem EGF-like repeats. Notch receptor is a signaling molecule that functions in cell development and differentiation. The Notch family includes several members for the receptor as well as ligand. Binding of ligand to a Notch receptor triggers the cleavage of the receptor at a site in the intracellular domain (ICD), releasing the activated form of the receptor which then migrates to the nucleus.

For men, prostate cancer is the second most fatal cancer after lung cancer. In advanced stages, prostate cancer metastasizes to the bone. Depending on the stage of the cancer, prostate cancer treatment involves one or a combination of the following therapies: surgery to remove the cancerous tissue, radiation therapy, chemotherapy, androgen deprivation (e.g., hormonal therapy) in the case of prostate cancer. The majority of patients who undergo hormone therapy progress to develop androgen-independent disease. Currently, there is no effective treatment for the 20–40% of prostate cancer patients who develop recurrent disease after surgery or radiation therapy, or for those in whom the cancer has metastasized at the time of diagnosis. Chemotherapy has its toxic side effects, especially in elderly patients. There is a need for new forms of prostate cancer therapy.

The present invention provides alternative methods of treating cancer that overcome the limitations of conventional therapeutic methods as well as offer additional advantages that will be apparent from the detailed description below.

SUMMARY OF THE INVENTION

In one embodiment, the invention concerns a method of decreasing the proliferation of prostate cancer cells by activating the Notch receptor.

In other embodiments, the invention provides for methods of detecting, diagnosing and alleviating prostate cancer by contacting biological samples suspected of prostate cancer. Detection and diagnosis of prostate cancer in the biological sample may include determining level of Notch expression, effects of Notch ligands on Notch receptor, or probing the biological sample with Notch receptor. Treatment may include contacting the biological sample with agonists to Notch 1 receptor or administration of a soluble Notch ligand.

In another embodiment, the invention provides an antibody which binds, preferably specifically, to Notch1. Optionally, the antibody is a monoclonal antibody, humanized antibody, antibody fragment or single-chain antibody.

Another embodiment of the invention concerns agonists and antagonists of Notch receptor as defined herein. In a particular embodiment, the agonist is an anti-Notch1 antibody, a soluble Notch1 ligand, or a small molecule.

In a still further embodiment, the invention concerns a method of identifying agonists to Notch receptor which comprise contacting the Notch receptor with a candidate molecule and monitoring a biological activity mediated by said Notch receptor. Preferably the Notch receptor is a native Notch receptor.

Another embodiment of the present invention is directed to the use of constitutively active Notch receptor, or an agonist thereof, for the preparation of a medicament useful in the treatment of a condition which is responsive to the constitutively active Notch receptor or an agonist thereof.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1A shows a TAQMAN™ RT-PCR analysis of Notch1 expression in rat prostate tissue.

FIG. 1B shows in situ hybridization of Notch1 expression in developing mouse prostate.

FIG. 2A shows Notch1 expression in the epithelium surrounding the lumen of the budded ductal epithelial units of prostate during development (P3) using a Notch1-GFP transgenic mouse model.

FIG. 2B shows Notch1 expression at developmental stage P12. The majority of cells in the epithelium are positive for Notch1-GFP signal.

FIG. 2C shows the cells in the basal layer of the epithelium showing weaker Notch1-GFP expression in the adult animal.

FIG. 2D1 shows Notch1-GEP expression in prostatic sections at developmental stage P19.

FIG. 2D2 shows prostatic sections taken from the Notch1-GFP transgenic mouse and labeled with a basal cell marker, anti-keratin 14.

FIG. 2D3 shows co-localization of Notch1 signal with Keratin 14 antibody staining, confirming that Notch1 is expressed in the basal cells of the prostate.

FIG. 3 shows a TAQMAN™ RT-PCR analysis of Notch1 in primary human prostate epithelial and prostatic cancer cells.

FIGS. 4A–4B shows in situ hybridization of normal prostate probed with Notch1 in the TRAMP mouse model.

FIGS. 4C–4D shows in situ hybridization of moderately differentiated adenocarcinoma cells probed with Notch1 in the TRAMP mouse model.

FIGS. 4E–4F shows in situ hybridization of prostate tumor cells which had metastasized to the lymph node probed with Notch1 in the TRAMP mouse model.

FIG. 4G shows staining for Keratin 14 in normal prostate in wild type mice.

FIG. 4H shows staining for Keratin 14 in a well differentiated carcinoma in the TRAMP mouse model.

FIG. 5A shows a TAQMAN™ analysis of 4 known Notch ligands.

FIG. 5B shows in situ hybridization of the Notch ligand Jagged1, in prostatic sections prepared from TRAMP mice and wild type mice.

FIG. 6A shows expression of a constitutively active form of Notch1 decreases cell proliferation.

FIG. 6B shows treatment of cells with a constitutively active form of Notch1 increases the expression of a CBF-1/luciferase construct.

DETAILED DESCRIPTION OF PREFERRED EMBODIMENTS

The invention encompasses several aspects. One aspect of the invention is a method of inhibiting or decreasing the proliferation of cancer cells by administering an agonist of Notch receptor which results in activation of Notch signaling. In a specific embodiment, the Notch receptor is Notch1 and the cancer is prostate cancer. Another aspect of the invention is a method of destroying cancer and tumor cells which express a Notch receptor by administering to a patient in need thereof, a therapeutically effective amount of a composition comprising a Notch receptor binding partner effective for that purpose. A further aspect of the invention is a method of alleviating cancer, in particular, prostate cancer, by administering an agonist of Notch receptor. For therapeutic applications, the activators of Notch signaling can be used alone, or in combination therapy with, e.g., hormones, antiangiogens, or radiolabeled compounds, or with surgery, cryotherapy, and/or radiotherapy.

The Notch receptor binding partner useful in destroying cancer cells, in particular prostate cancer cells, includes soluble ligands of the receptor, antibodies and fragments thereof, and small molecules that bind the Notch receptor. The binding partners can be conjugated to a cytotoxic agent. The antibodies are preferably internalizing and/or growth inhibitory antibodies. The cytotoxic agent can be a toxin, antibiotic, radioactive isotope or nucleolytic enzyme. A preferred cytotoxic agent is a toxin, preferably a small molecule toxin such as calicheamicin or a maytansinoid.

In all the above embodiments, the cancer includes are as described below. In a preferred embodiment, the cancer is prostate cancer.

In all the above embodiments, the soluble ligand includes truncated forms of the native or natural ligand lacking the transmembrane domain, and immunoglobulin fusions of these soluble ligands where, e.g., the soluble ligand is fused to the Fc portion of an IgG. Other than the truncation, the soluble ligand can have further amino acid variation from the native sequence. These amino acid variants of the native ligand can, in the portion of the sequence that corresponds to the native sequence, have one or more amino acid changes. These amino acid changes can, e.g., confer upon the ligand, ability to constitutively activate the Notch receptor, greater binding, longer half-life and greater stability in vivo.

The agonists and binding partners of Notch receptor can be synthetically or recombinantly produced or otherwise isolated.

The invention also provides agonists of Notch receptor that inhibit or decrease cancer cell growth or proliferation. Also provided are compositions comprising one or more agonists of Notch receptor effective for use in the aforementioned methods, and a carrier. A Notch receptor agonist includes any molecule that can produce an activated signaling form of the receptor, including soluble ligands of the receptor, antibodies and fragments thereof, small molecules that bind the Notch receptor extracellularly or that can enter the cell and act intracellularly, and molecules that have enzymatic activity in cleaving the receptor to release the activated form. In a preferred embodiment, the antibody in the composition is a humanized antibody. In a preferred embodiment, the carrier is a pharmaceutically-acceptable carrier. The compositions can be provided in an article of manufacture or a kit.

Another aspect of the invention is an isolated nucleic acid encoding an internalizing or cytotoxic anti-Notch receptor antibody of the invention, as well as a vector comprising the nucleic acid. The human Notch1 DNA sequence can be found using GenBank Accession Number HUMTAN1. Also provided by the invention are cells including *E. coli* and hybridomas that produce the above-described antibodies.

"Notch" encompasses all members of the Notch receptor family and in particular, Notch1.

An "agonist" of Notch receptor in addition to binding Notch receptor, has a direct effect on a Notch receptor bearing cell. The Notch receptor agonist will bind Notch receptor, and as well, initiate or mediate the signaling event associated with the Notch receptor, such as, for example, to cause the intracellular domain of Notch to be cleaved and translocated to the nucleus. Here it induces the synthesis of transcriptional repressors known as HES-1. When ECD truncated forms of Notch are tested, the HES-1 promoter is strongly stimulated. Activation of the HES-1 promoter can be assayed in vitro. The ability to induce Notch receptor activation can be quantified using techniques known in the art such as reporter constructs such as Beta-galactosidase, chloramphenicol acetyl transferase (CAT) or luciferase.

The proliferation of cancer cells is reduced or arrested when the Notch receptor is activated by contact with an added or administered Notch receptor agonist or activator, compared to situation in the absence of agonist Proliferation assays are described below The Notch ligands include Jagged1, Jagged2, Delta and Delta4.

Prostate cancer specifically includes prostate adenocarcinoma and related metastases.

The term "amino acid sequence variant" refers to a polypeptide that has amino acid sequences that differ to some extent from a native sequence polypeptide. Ordinarily, amino acid sequence variants of Notch receptor will possess at least about 70% homology with the native sequence Notch receptor, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Notch polypeptide natural environment will not be present. Ordinarily, however, isolated polypeptide will be prepared by at least one purification step The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobutin" (Ig) is used interchangeably with "antibody" herein. An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851–6855 (1984)). Chimeric antibodies of interest herein include "primatized" antibodies comprising variable domain antigen-binding sequences derived from a non-human primate (e.g. Old World Monkey, Ape etc), and human constant region sequences.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10):1057–1062 [1995]); single-chain antibody molecules; and multispecific antibodies formed from antibody fragments.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994); Borrebaeck 1995, infra.

The term "diabodies" refers to small antibody fragments prepared by constructing sFv fragments (see preceding paragraph) with short linkers (about 5–10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444–6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al., *Nature* 332:323–329 (1988); and Presta, *Curr. Op. Struct. Biol.* 2:593–596 (1992).

The word "label" when used herein refers to a detectable compound or composition which is conjugated directly or indirectly to the antibody so as to generate a "labeled" antibody. The label may be detectable by itself (e.g. radio-isotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The term "epitope tagged" when used herein refers to a chimeric polypeptide comprising a polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

An anti-Notch receptor antibody that "internalizes" is one that is taken up by (i.e., enters) the cell upon binding to cell surface Notch on a mammalian cell. The internalizing antibody will of course include antibody fragments, human or humanized antibody and antibody conjugate. For therapeutic applications, internalization in vivo is contemplated. The number of antibody molecules internalized will be sufficient or adequate to kill a Notch-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugate to the antibody is sufficient to kill the tumor cell. Whether an antibody internalizes upon binding Notch on a mammalian cell can be determined by various assays e.g., by confocal or electron microscopy using fluorescent or radiolabeled antibody.

An "antibody that inhibits the growth of cancer cells expressing Notch receptor or a "growth inhibitory" antibody is one which binds to and results in measurable growth inhibition of cancer cells expressing or overexpressing Notch receptor. Preferred growth inhibitory anti-Notch receptor antibodies inhibit growth of Notch receptor expressing tumor cells (e.g., prostate cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 µg/ml or about 0.5 nM to 200 nM in cell culture. where the growth inhibition is determined 1–10 days after exposure of the tumor cells to the antibody The antibody is growth inhibitory in vivo if. e.g., administration of the anti-Notch receptor antibody at about 1 µg/kg to about 100 mg/kg body weight results in reduction in tumor size or tumor cell proliferation within about 5 days to 3 months from the first administration of the antibody, preferably within about 5 to 30 days.

The terms "cancer" and "cancerous" refer to or describe the physiological condition in mammals that is typically characterized by unregulated cell growth. Examples of cancer include. but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer. bladder cancer, hepatoma, breast cancer, colon cancer, rectal cancer, colorectal cancer, endometrial or uterine carcinoma, salivary gland carcinoma, kidney or renal cancer. prostate cancer, vulval cancer, thyroid cancer, hepatic carcinoma, anal carcinoma, penile carcinoma, as well as head and neck cancer.

A "Notch receptor-expressing cancer" is a cancer comprising cells that have Notch receptor protein present on the cell surface. A "Notch receptor-expressing cancer" produces sufficient levels of Notch receptor on the surface of cells thereof, such that a Notch receptor agonist or antibody can bind thereto and have a therapeutic effect with respect to the cancer. A cancer which "overexpresses" Notch receptor is one which has significantly higher levels of Notch receptor at the cell surface thereof, compared to a noncancerous cell of the same tissue type. Notch receptor overexpression may be determined in a diagnostic or prognostic assay by evaluating increased levels of the Notch receptor protein present on the surface of a cell (e.g. via an immunohistochemistry assay; FACS analysis). Alternatively, or additionally, one may measure levels of Notch receptor-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study Notch receptor overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991: U.S. Pat. No. 5,401,638 issued Mar. 28, 1995; and Sias et. al. *J. Immunol. Methods* 132: 73–80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

"Alleviation of cancer" refers to both therapeutic treatment and prophylactic or preventative measures, wherein the object is to prevent or slow down (lessen) the targeted pathologic condition or disorder. Those in need of alleviation include those already with the disorder as well as those prone to have the disorder or those in whom the disorder is to be prevented. A subject or mammal is "alleviated" for a Notch receptor-expressing cancer if, after receiving a therapeutic amount of a Notch receptor agonist according to the methods of the present invention, the patient shows observable and/or measurable reduction in or absence of one or more of the following: reduction in the number of cancer cells or absence of the cancer cells, reduction in the tumor size; inhibition (i.e., slow to some extent and preferably stop) of cancer cell infiltration into peripheral organs; inhibition (i.e., slow to some extent and preferably stop) of tumor metastasis; inhibition, to some extent, of tumor growth; and/or relief to some extent, one or more of the symptoms associated with the specific cancer, and reduced morbidity and mortality. To the extent the Notch receptor agonist or antibody may prevent growth and/or kill existing cancer cells, it may be cytostatic and/or cytotoxic. Reduction of these signs or symptoms may also be felt by the patient.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). For prostate cancer, the progress of therapy can be assessed by routine methods, usually by measuring serum PSA (prostate specific antigen) levels; the higher the level of PSA in the blood, the more extensive the cancer. Commercial assays for detecting PSA are available, e.g, Hybritech Tandem-E™ and Tandem-R™ PSA assay kits, the Yang ProsCheck™ polyclonal assay (Yang Labs, Bellevue, Wash.), Abbott Imx™ (Abbott Labs, Abbott Park, Ill.), etc. Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The term "therapeutically effective amount" refers to an amount of an agonist, antibody or a drug effective to "alleviate" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "alleviating". To the extent the drug may prevent growth and/or kill existing cancer cells, it may be cytostatic and/or cytotoxic.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albuntin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Mammal" for purposes of treatment refers to any animal classified as a mammal, including humans, domestic and farm animals, and zoo. sports or pet animals such as dogs, cats, cattle, horses, sheep, pigs, goats, rabbits etc. Preferably, the mammal is human.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal. plant or animal origin, including fragments and/or variants thereof, and the various anti-tumor or anticancer agents disclosed below. Other cytotoxic agents are described below.

A "growth inhibitory agent" when used herein refers to a compound or composition which inhibits growth of a cell, especially a Notch receptor expressing cancer cell, either in vitro or in Vivo. Thus, the growth inhibitory agent may be one which significantly reduces the percentage of Notch receptor expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and anti-neoplastic drugs" by Murakami et al. (WB Saunders: Philadelphia, 1995), especially p. 13.

A "small molecule" is defined herein to have a molecular weight below about 500 Daltons.

An "isolated nucleic acid" is a nucleic acid, e.g., an RNA, DNA, or a mixed polymer, which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary regulatory elements for expression of the antibodies including antibody fragment of the invention, in bacterial or eukaryotic cells.

A "liposome" is a small vesicle composed of various types of lipids, phospholipids and/or surfactant which is useful for delivery of a drug (such as a Notch polypeptide or antibody thereto) to a mammal. The components of the liposome are commonly arranged in a bilayer formation, similar to the lipid arrangement of biological membranes.

The Notch receptor agonists and prostate cancer cell growth inhibitory antibodies of the invention also have various non-therapeutic applications. In view of the fact that the use of PSA as a tool for screening or diagnosing prostate cancer is controversial, the agonists and antibodies of the present invention can be useful for diagnosis and staging of Notch-expressing cancers (e.g., in radioimaging). The antibodies are also useful for purification or immunoprecipitation of Notch from cells, for detection and quantitation of Notch in vitro, e.g. in an ELISA or a Western blot, to kill and eliminate Notch-expressing cells from a population of mixed cells as a step in the purification of other cells.

The Notch receptor agonists and antibodies can be fused to a heterologous polypeptide sequence. The antibody can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism.

The present Notch receptor agonists and antibodies are useful for treating a Notch receptor expressing cancer or alleviating one or more symptoms of the cancer in a mammal. Such a cancer includes prostate cancer and leukemias. The antibody is able to bind to at least a portion of the cancer cells that express Notch receptor in the mammal and preferably is one that does not induce or that minimizes HAMA response (human anti-mouse antibody). In a preferred embodiment, the antibody is effective to destroy or kill Notch receptor-expressing tumor cells or inhibit the growth of such tumor cells, in vitro or in vivo, upon binding to Notch receptor on the cell. Such an antibody includes a naked anti-Notch receptor antibody (not conjugated to any agent). Naked antibodies that have cytotoxic or cell growth inhibition properties can be further harnessed with a cytotoxic agent to render them even more potent in tumor cell destruction.

Cytotoxic properties can be conferred to an anti-Notch receptor antibody by, e.g., conjugating the antibody with a cytotoxic agent, to form an immunoconjugate as described below. The cytotoxic agent or a growth inhibitory agent is preferably a small molecule. Toxins such as calicheamicin or a maytansinoid and analogs or derivatives thereof, are preferable.

PRODUCTION OF ANTI-NOTCH-1 ANTIBODIES (i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobutin, or soybean trypsin inhibitor, using a bifunctional or derivatuzing agent, e.g., maleimidobenzoyl sulfosuccinimide ester (conjugation through cysteine residues). N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, Immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the liter plateaus. Conjugates also can be made in recombinant cell culture as protein fusions. Also, aggregating agents such as alum are suitably used to enhance the immune response.

(ii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myelorna cell line using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium). which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8–653 cells available from the American Type Culture Collection, Rockville, Md. USA. Human mycloma and mouse-human beteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. such as radioimmunoassay (RIA) or enzyme-linked immunosorbent assay (ELISA).

The binding affinity of the monoclonal antibody can, for example, be determined by the Scatchard analysis described in Munson et al., *Anal, Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose™) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Pluckthun, *Immunol. Revs.*, 130:151–188 (1992).

In a further embodiment, monoclonal antibodies or antibody fragments can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA that encodes the antibody may be modified, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA*, 81:6851 (1984)), or by fusing the immunoglobulin coding sequence with all or part of the coding sequence for a non-immunoglobulin polypeptide. The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Reichmann et al., *Nature*, 332:323–327 (1988); Verhoeyen et al., *Science*, 239:1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad Sci. USA*, 89:4285 (1992); Presta et al, *J. Immunol.*, 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, Le., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Notch receptor antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl Acad. Sci. USA*, 90:2551 (1993); Jakobovits et al., *Nature*, 362:255–258 (1993); Bruggemann et al., *Year in Immuno.*, 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552–553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564–571 (1993). Several sources of V-gene segments can be used for phage display. Clackson et al., Nature, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including selfantigens) can be isolated essentially following the techniques described by Marks et al., J. Mol. Biol. 222:581–597 (1991), or Griffith et al., EMBO J. 12:725–734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

(v) Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107–117 (1992); and Brennan et al., Science, 229:81 (1985)). However, these fragments can now be produced directly by recombinant host cells. Fab, Fv and ScFv antibody fragments can all be expressed in and secreted from E. col, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163–167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the Notch receptor protein. Other such antibodies may combine a Notch receptor binding site with a binding site for another protein. Alternatively, an anti-Notch receptor arm may be combined with an arm which binds to a triggering molecule on a leukocyte such as a T-cell receptor molecule (e.g. CD3), or Fe receptors for IgG (FcγR), such as FcγRI (CD64), FeγRII (CD32) and FcγRIII (CD16), so as to focus and localize cellular defense mechanisms to the Notch receptor-expressing cell. Bispecific antibodies may also be used to localize cytotoxic agents to cells which express Notch receptor. These antibodies possess a Notch receptor-binding arm and an arm which binds the cytotoxic agent (e.g. saporin, anti-interferon-γ, vinca alkaloid, ricin A chain, methotrexate or radioactive isotope hapten). Bispecific antibodies can be prepared as full length antibodies or antibody fragments (e.g. F(ab')$_2$bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcγ antibody is shown in WO98102463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655–3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination. According to another approach described in U.S. Pat. No. 5,731,168, the interface between a pair of antibody molecules can be engineered to maximize the percentage of heterodimers which are recovered from recombinant cell culture. The preferred interface comprises at least a part of the $CH_3$ domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad Sci. USA*, 90:6444–6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol*, 152:5368 (1994).

Antibodies with more than two valencies are contemplated. For example, trispecific antibodies can be prepared. Tutt et al. *J. Immunol.* 147: 60 (1991).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

(viii) Screening for Antibodies with the Desired Properties

Techniques for generating antibodies have been described above. One may further select antibodies with certain biological characteristics, as desired. The growth inhibitory effects of an anti-Notch receptor antibody of the invention may be assessed by methods known in the art, e.g., using cells which express Notch receptor either endogenously or following transfeetion with the Notch receptor gene. For example, the tumor cell lines and Notch receptor-transfected cells may treated with an anti-Notch receptor monoclonal antibody of the invention at various concentrations for a few days (e.g., 2–7) days and stained with crystal violet or MTT or analyzed by some other calorimetric assay. Another method of measuring proliferation would be by comparing $^3$H-thymidine uptake by the cells treated in the presence or absence an anti-Notch receptor antibody of the invention. After antibody treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Preferably, the Notch receptor agonist will inhibit cell proliferation of a Notch receptor-expressing tumor cell in vitro or in vivo by about 25–100% compared to the untreated tumor cell, more preferably, by about 30–100%, and even more preferably by about 50–100% or 70–100%, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1–10 days after exposure of the tumor cells to the antibody. The antibody is growth inhibitory in vivo if administration of the anti-Notch receptor antibody at about 1 μg/kg to about 100 mg/kg body weight results in reduction in tumor size or tumor cell proliferation within about 5 days to 3 months from the first administration of the antibody. preferably within about 5 to 30 days.

Maytansine and Maytansinoids

In one preferred embodiment, an anti-Notch receptor antibody (full length or fragments) of the invention is conjugated to one or more maytansinoid molecules.

Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307.016: 4,308,268; 4,308,269; 4,309,428; 4,313,946;

4,315,929; 4.317,821; 4,322,348; 4,331.598; 4,361,650; 4,364,866; 4,424,219; 4,450,254; 4,362,663; and 4,371,533, the disclosures of which are hereby expressly incorporated by reference.

The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Notch receptor antibodies. Examples include $At^{211}$, $I^{131}$, $I^{125}$, $Y^{90}$, $Re^{186}$, $R^{188}$, $Sm^{153}$, $Bi^{212}$, $p^{32}$, $pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et at (1978) Biochem. Biophys. Res. Commun. 80: 49–57 can be used to incorporate iodine-123. "Monoclonal Antibodies in Immunoscintigraphy" (Chatal,CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238. 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. *Cancer Research* 52: 127–131 (1992); U.S. Pat. No. 5,208,020) may be used.

Alternatively, a fusion protein comprising the anti-Notch receptor antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as␣8-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity. also known in the art as "abzymes", can be used to convert the prodrugs of the invention into free active drugs (see, e.g., Massey, *Nature* 328: 457–458 (1987)). Antibody-abzyme conjugates can be prepared as described herein for delivery of the abzyme to a tumor cell population.

The enzymes of this invention can be covalently bound to the anti-Notch receptor antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et at., *Nature*, 312: 604–608 (1984).

(xi) Other Antibody Modifications

Other modifications of the antibody are contemplated herein. For example, the antibody may be linked to one of a variety of nonproteinaceous polymers, e.g., polyethylene glycol. polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's *Pharmaceutical Sciences*, 16th edition, Oslo, A., Ed., (1980).

(ix) Purification of Anti-Notch Receptor Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicofin™ or Millipore Pellicon™ ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62:1–13 (1983)). Protein G is recommended for all mouse isotypes and for human $\gamma 3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5–4.5. preferably performed at low salt concentrations (e.g., from about 0–0.25M salt).

PHARMACEUTICAL FORMULATIONS

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride. benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5–200 mg/ml, preferably between 10–100 mg/ml.

The formulation herein may also contain more than one active compound as necessary for the particular indication being treated, preferably those with complementary activities that do not adversely affect each other. For example, in addition to the anti-Notch receptor antibody which internalizes, it may be desirable to include in the one formulation, an additional antibody, e.g. a second anti-Notch receptor antibody which binds a different epitope on Notch receptor, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such, molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

In one particular embodiment, an immunoconjugate comprising the anti-Notch receptor antibody conjugated with a cytotoxic agent is administered to the patient. Preferably, the immunoconjugate bound to the Notch receptor protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-Notch receptor antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-Notch receptor antibody. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Notch receptor antibody or antibodies, with administration of an antibody directed against another tumor antigen associated with the particular cancer.

ADMINISTRATION OF ANTI-NOTCH RECEPTOR AGONISTS AND ANTIBODIES

In another embodiment, the antibody therapeutic treatment method of the present invention involves the combined administration of an anti-Notch receptor antibody (or antibodies) and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Notch receptor antibody (and optionally other agents as described herein) may be administered to the patient.

For the prevention or treatment of disease, the dosage and mode of administration will be chosen by the physician according to known criteria. The appropriate dosage of antibody wilt depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g. about 0.1–15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Notch receptor antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

ARTICLES OF MANUFACTURE AND KITS

Another embodiment of the invention is an article of manufacture containing materials useful for the alleviation of anti-Notch receptor expressing cancer, in particular prostate cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for alleviating the cancer condition and may have a sterile access port (for example the container may be an intravenous solution bag or a vial having a stopper pierceable by a hypodermic injection needle). At least one active agent in the composition is an anti-Notch receptor antibody of the invention. The label or package insert indicates that the composition is used for treating prostate cancer, androgen independent prostate cancer, or androgen dependent prostate cancer, or bladder cancer. The label or package insert will further comprise instructions for administering the agonist or antibody composition to the cancer patient.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for Notch receptor cell killing assays, for purification or immunoprecipitation of Notch receptor from cells. For isolation and purification of Notch receptor, the kit can contain an anti-Notch receptor antibody coupled to beads (e.g., sepharose beads). Kits can be provided which contain the antibodies for detection and quantitation of Notch receptor in vitro, e.g. in an ELISA or a Western blot. As with the article of manufacture, the kit comprises a container and a label or package insert on or associated with the container. The container holds a composition comprising at least one anti-Notch receptor antibody of the invention. Additional containers may be included that contain, e.g., diluents and buffers, control antibodies. The label or package insert may provide a description of the composition as well as instructions for the intended in vitro or diagnostic use.

EXAMPLES

EXAMPLE 1
Expression of Notch1 During Prostatic Development

To determine if Notch1 is expressed in the prostate and if it plays a role in the developing prostate, TAQMAN™ quantitative RT-PCR was performed using RNA extracted from whole mount prostate organs prepared from rats at different developmental stages. Prostatic tissue was dissected from rats at developmental stages postnatal day 1 (P1), postnatal day 10 (P10) and adult, placed in lysis buffer and homogenized through a Qiashredder™ column (Qiagen, Valencia Calif.). Total RNA was immediately isolated using the RNeasy™ protocol from (Qiagen, Valencia Calif.). The rat housekeeping gene, gapdh, was used as a control and experimental results of interest were normalized to gapdh expression levels. Rat gapdh primer sequences are reported in Zheng et al., (1999) Journal of Neurocytology. 28:901–9 12. Initial RT-PCR amplifications were confirmed by agarose gel electrophoresis to ensure that the reaction products were the correct molecular weights. The primers/probes for rat Notch1 are as follows:

Rat Notch1 Primer Set

```
Forward primer
5' GGAGAGGCTGCCAAGGTTTT 3'     SEQ ID NO.1

Reverse primer
5' GCAAATTGGCCGTCAGGA 3'       SEQ ID NO.2

Probe
5' CGGCTTCCAAGTGGTGCCGG 3'     SEQ ID NO.3
```

Results

Notch1 is expressed at high levels in the developing prostate at postnatal day 1 to postnatal day 10 (P1 to P10). Notch1 expression was downregulated in the adult. These results are shown graphically in FIG. 1A.

Example 2
Notch1 Expression is Associated with the Basal Epithelial Cells

Labeled sense and antisense riboprobes were generated from PCR products cloned into transcription vectors. The murine Notch1 CDNA was cloned in pBluescript (Stratagene, La Jolla Calif.) and probe spanned from nucleotides 3773 to 4639 (866 bp) of the mouse Notch1 sequence. For the murine Notch1 sequence see GenBank accesssion Z1886. Primers included extensions encoding 27-nucleotide T7 or T3 RNA polymerase initiation sites to allow in vitro transcription of sense or antisense probes, respectively, from the amplified products (Lu et al. Cell Vision 1994, 1:169–176). Five $\mu$m thick sections were deparaffinized, deproteinated in 4 $\mu$g/ml of proteinase K for 30 minutes at 37° C., and further processed for in situ hybridization. $^{33}$P-UTP labeled sense and antisense probes were hybridized to the sections at 55° C. overnight. Unbound probe was removed by incubation in 20 mg/ml RNase A for 30 minutes at 37° C., followed by a high stringency wash at 55° C. in 0.1× SSC for 2 hours and dehydration through graded concentrations of ethanol. The slides were dipped in NBT2 nuclear track emulsion (Eastman Kodak), exposed in sealed plastic slide boxes containing desiccant for 4 weeks at 4° C., developed and counterstained with hematoxylin and eosin. The in situ hybridization was routinely performed on duplicate sections with sense and antisense probes.

Results

The in situ hybridization was used to determine whether Notch1 is expressed by epithelial cells or stromal cells in the prostate. Notch1 signal was seen specifically in epithelial, but not in stromal cells at both postnatal day 3 (P3) and postnatal day 16 (P16). This is shown graphically in FIG. 1B.

Example 3
Notch1 Expression in Basal Epithelial Cells

In Example 2, radioactive in situ hybridization experiments showed restricted Notch1 expression patterns in prostate epithelium, but it does not provide the resolution to distinguish which epithelial cell type specifically expressed Notch1. To precisely determine the expression pattern of Notch1 in the prostate epithelium, prostate tissue sections were taken from transgenic mice which expressed the marker gene for green fluorescence protein (GFP) under the control of the Notch1 promoter. In this transgenic mice, the cells expressing Notch1 fluoresce green. A comparison of Notch1-GFP mice with in situ hybridization for Notch1 was performed and reported in the literature (Lewis et al., Mechanisms of Development (1998)78:159–163).

Results

At postnatal day 3 (P3), there was robust GFP signal in the epithelium surrounding the lumen of the budded ductal epithelia. At this developmental stage, all of the cells in the epithelium were labeled, and showed a typical barrel-shaped morphology extending from the base to the lumen (FIG. 2A). At postnatal day 12 (P12), the majority of the cells in the epithelium were still GFP positive, some had lost GFP signal (FIG. 2B). In the adult, GFP labeling became much weaker, and only a small fraction of cells in the deep, basal layer of the epithelium were GFP positive. The GFP-positive cells in the adult prostate displayed a small, round cell body with thin processes instead of a columnar or barrel-like shape (FIG. 2C).

To confirm the basal cell identity of the GFP-positive cells in the prostate, the prostatic sections were additionally labeled with a basal cell marker, anti-cytokeratin 14 antibody. (Hayward et al., (1996) Acta Anatomica 155:81–93). About all GFP-positive cells were also labeled by the anti-cytokeratin 14 antibody, thus confirming the basal cell type (FIG. 2D2). The P19 Notch1-GFP and Notch1-GFP/cytokeratin 14 results are shown in FIGS. 2D1–2D3.

Example 4
Notch1 is Expressed in Prostate Cancer Cells

The pattern of Notch1 in prostate cancer cells was determined by performing TAQMAN™ analysis on RNA extracted from the prostate cancer cell lines DU145, LNCaP, PC3 and the prostatic epithelial cell line PrE™ (Clonetics, Walkersville Md.). Total RNA was isolated from these cell lines using the RNAzol™ protocol (Tel-Test, Friendswoods Tex.), treated with DNase I, (Roche Molecular (BMB)) for 30 minutes at room temperature, and then purified using the RNeasy™ protocol (Qiagen, Valencia Calif.). First strand synthesis was performed using M-MLV reverse transcriptase (Gibco BRL, Gaitherburg Md.). This first strand synthesis was then analyzed by TAQMAN™ PCR analysis, again using gapdh as a control for expression levels. The human Notch1 DNA sequence can be found using GenBank Accession Number HUMTAN 1. The primers used for Notch1 are as follows:

```
Human Notch 1 Primer Set
Forward Primer
5' CAGTGTGGGCGGGTCC 3'         SEQ ID NO.4
```

-continued

```
Reverse Primer
5' GTTGTATTGGTTCGGCACCAT 3'           SEQ ID NO.5

Probe
5' CCGCTCTGCAGCCGGGACA 3'             SEQ ID NO.6

Human Gapdh Primer Set
Forward Primer
5' CTCCTCCACCTTTGACGCTG 3'            SEQ ID NO.7

Reverse Primer
5' CATACCAGGAAATGAGCTTGACAA 3'        SEQ ID NO.8

Probe
5' CTGGCATTGCCCTCAACGACCAC 3'         SEQ ID NO.9
```

Results

Notch1 was found to be expressed highly in LNCaP cells, but very low in DU145 cellsPC3 cells showed moderate expression. The levels of Notch1 expression were highest in PrE cells. This result is shown graphically in FIG. 3.

Example 5
Notch1 Expression is Elevated in Malignant and Metastatic Prostatic Tumor Cells in a TRAMP Mouse Model One well established animal model for human prostate cancer is the Transgenic Adenocarcinoma of the Mouse Prostate™ (TRAMP™) (Greenberg N. Mex., 1995, PNAS 92:3439–43). Though there are significant anatomical differences in the mouse prostate compared to that of the human, there are inherent common characteristics including secretory function and hormonal regulation. In the TRAMP™ model, the minimal promoter of the rat probasin gene targets expression of the SV40large T- antigen to the prostatic epithelium. All male TRAMP mice progress to prostate cancer usually by 8–12 weeks (Gingrich J R et al., 1997, Cancer Research 57:4687–91). The autochthonous TRAMP™ model is particularly relevant to human prostate carcinoma in that the development of the cancer is specific to the prostatic epithelium and is initially regulated by androgens. Furthermore. metastases to distant sites eventually occur (Gingrich J R et al., 1996, Cancer Research 56:4096–102; Gingrich J R et al , 1999, Prostate Cancer & Prostatic Diseases 2:70–75).

Male and female adult CD-1 mice between the ages of 10 and 24 weeks were obtained form Charles River laboratories. Pregnant mice were ordered for the collection of embryos. The day of isolation with copulatory plug was considered day 1 of embryonic development. Fetal tissues examined by ISH included: E10, E13, E14. E15, E17 and E18. Adult tissues examined included: tissues of the male urogenital system, female urinary bladder and kidney, pubescent mammary gland, 14 day pregnant mammary gland, lactating mammary gland, liver, heart, skin and intestine. AU tissues were fixed in 4% formalin and paraffin-embedded. Breeder pairs of TRAMP™ transgenic mice were obtained from Dr. Norman Greenberg (Baylor College of Medicine, Houston, Tex.) Urogenital tissues from wild type litter, mate C57BL/6 were taken at age 12 and 24 for comparison to age matched TRAMP™ transgenic mice. By the age of 12 weeks, TRAMP™ mice have typically progressed to PIN and or well differentiated tumors. TRAMP™ male mice between the ages of 12 to 39 weeks of age were sacrificed and tissues were collected for routine histology and ISH studies. The histological grade of prostate cancer was determined in according to previously published studies in the TRAMP™ model (Gingnch J R et al., 1999, Prostate Cancer & Prostatic Diseases 2:70–75).

Results

This set of experiments were performed to determine if there was any change in the levels of Notch1 expression in the TRAMP™ mouse prostate, specifically, in malignant cells during prostatic tumorigenesis. In situ hybridization of the tissues from TRAMP™ mice demonstrated that normal prostate expressed undetectable levels of Notch1 (FIGS. 4A, 4B). In contrast, moderately-differentiated adenocarcinoma cells (FIGS. 4C, 4D), poorly differentiated adenocarcinoma cells, and some areas of prostatic intraepithelial neoplasia (PIN) expressed high levels of Notch1. The prostate tumor cells which had metastasized to the lymph node also expressed markedly higher levels of Notch1 when compared to the neighboring normal tissue (FIGS. 4E, 4F).

Because Notch1 expression is associated with basal cell population during prostatic development, the finding that Notch expression is upregulated in the malignant cells in the TRAMP™ prostate raises a question whether these malignant cells possess basal cell futures. Immunohistochemistry was done using anti-cytokeratin 14 antibody, a basal cell marker, in prostatic tissue prepared from the TRAMP™ and wild type mice. It was found that the most majority of the cells were cytokeratin 14 negative in the PIN (data not shown) and well-moderately-differentiated TRAMP™ carcinomas (FIG. 4H), even though a small number of cytokeratin 14 positive cells were observed. There was no apparent increase in the number of cytokeratin 14 positive cells in the PIN and adenocarciomas of the TRAMP™ mice as compared to the normal prostate in wild type mice (FIG. 4G). In fact, in moderately- and poorly-differentiated carcinomas of the TRAMP™, virtually all cells were cytokeratin 14 negative (Data not shown). These results show that in the malignant cells of the TRAMP™ Notch1 expression is uncoupled from cytokeratin 14 expression. cells of the TRAMP, Notch1 expression is uncoupled from cytokeratin 14 expression.

Example 6
Expression Levels of Notch1 Ligands in Prostate Cancer Cells

As ligands for Notch1 activate the receptor. it is necessary to understand if Notch1 ligands are also expressed in prostatic cancer cells. Therefore, TAQMAN™ analysis was performed for four Notch1 ligands, Jagged1, Jagged2, Delta and Delta4. RNA for this experiment was isolated as described in Example 4.

```
Jageed1 Primer Set
Forward Primer
5' CAACCGCATCGTGCTGC 3'               SEQ ID NO.10

Reverse Primer
5' CGCCTCCACAAGCAACGTAT 3'            SEQ ID NO.11

Probe
5' CCTCGGCCAGGCGAAACTGAAA 3'          SEQ ID NO.12

Jageed2 Primer Set
Forward Primer
5' CGCTGTATGAAAGGAGAGAGCAA 3'         SEQ ID NO.13

Reverse Primer
5' CCGAGTGAGGAATAAAAGGAAGATT 3'       SEQ ID NO.14

Probe
5' TGCACAACCTCTGGTAACAAACGCGA 3'      SEQ ID NO.15

Delta Primer Set
Forward Primer
5' TGTGTGACGAACACTACTACGGAG 3'        SEQ ID NO.16
```

-continued

```
Reverse Primer
5' GTGAAGTGGCCGAAGGCA 3'              SEQ ID NO.17

Probe
5' TTCTGCCGTCCCCGGGACG 3'             SEQ ID NO.18

Delta4 Primer Set
Forward Primer
5' CTGGAGCTCAGCGAGTGTGAC 3'           SEQ ID NO.19

Reverse Primer
5' GCCATCCTCCTGGTCCTTAC 3'            SEQ ID NO.20

Probe
5' ACCCCTGTCGCAATGGAGGCAG 3'          SEQ ID NO.21
```

Results

Jagged1 was expressed in PrE cells and at low levels in LNCaP cells. Jagged2 was expressed at low levels in LNCaP cells, and Delta and Delta4 expression was low to undetectable in all four types of cells examined. This is shown graphically in FIG. 5A.

The expression profile of Jagged1 was confirmed using in situ hybridization (see Example 2 for conditions) with prostatic sections prepared from the TRAMP mouse model (see Example 5 for the TRAMP mouse model description). A strong hybridization signal was detected in the endothelial cells of blood vessels in normal and malignant prostate tissues. No signal was seen in the malignant epithelial cells in TRAMP tumors. This data is shown in FIG. 5B.

EXAMPLE 7

Activation of Notch1 Leads to a Decrease in Proliferation of Prostate Cancer Cells Notch1 expression is found in cancer cells, but Notch1 ligand expression appears relatively low. The activation of a Notch1 signal may influence the growth of prostate cancer cells. Various prostate cancer cell lines were transfected with a constitutively active form of Notch1, mN1-IC, which is the intracellular domain of mouse Notch1. The characteristics of this active form of Notch1 has been previously reported (Nyc et al., (1994) Development 120: 2424–2430). To measure DNA synthesis, and identical number of cells ($4\times10^3$ cells/well) were plated in 96-well plates in serum free prostate epithelial cell culture medium (PrEGM, Clonetics, Walkersville Md.). In this case the PrEGM medium was used without triiodothyronine, hydrocortisone. epinephrine and human recombinant EGF. $^3$H-thymidine (1 $\mu$Ci/well) was added 24 hours after seeding (he cells and incubated for 21 hours. Cells were trypsinized and then harvested using a Tomtec cell harvester. Cpm/well was then counted with a microplate scintillation counter (Packard Instrument Company ). Data was collected from 5 or 24 culture wells from each of the experimental groups and expressed as a mean +/–standard deviation. Two tailed, unpaired T-test was used to analyze the results statistically.

Results

Expression of the constitutively active form of Notch1 inhibited DNA synthesis in all of the prostate cancer cell lines examined, including DU145, LNCaP and PC3 cells. There was a statistically significant reduction in the proliferation rates in all 3 of the prostate cancer cell lines as compared to those transfected with a control vector. This data is shown graphically in FIG. 6A.

EXAMPLE 8

Activation of Notch1 Leads to CBF1 Activation

CBF1 is a DNA binding protein that has been described as an intracellular mediator of Notch signaling in mammals (Honjo et al., (1996) Genes Cells 1: 1–9). CBFI activated by Notch1 can lead to inhibition of neurogenesis (Artavanis-Tsakonas et al., (1995) Science 268: 225–232) and muscle cell differentiation (Notziger et al., (1999) Development 126:689–702). Dual luciferase assays indicate that activation of Notch signaling in LNCaP and PC3 cells transactivate CBF1 pathway. Cells were seeded in a 12-well tissue culture plate, and co-transfected the next day with CBF1-luciferase construct (194 ng) and the pRL-TK plasmid (6 ng) expressing Renilla luciferase, together with 800 ng mN1-IC plasmid or a control vector (pcDNA3). Fort-eight hours after transfection, cells were assayed for standard dual-luciferase activity according to manufacturer's instruction (Promega, Madison Wis.). Data are expressed as means of the relative luciferase units and standard deviations from three independent experiments.

Results

Using a CBF1/luciferase reporter gene construct in a co-transfection with the mN1-IC activated Notch1 construct, it was determined that there was a 300 fold increase in luciferase activity in cultured PC3 cells and a 1900 fold increase in LNCaP cells when compared to control transfections. These results are shown graphically in FIG. 6B.

Example 9

Expression of Notch in *E. coli*

This example illustrates preparation of an unglycosylated form of Notch by recombinant expression in *E. coli*.

The DNA sequence encoding Notch is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the Notch coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on After culturing the cells for several more hours, the cells can be harvested by centrifugation. The cell pellet obtained by the centrifugation can be solubilized using various agents known in the art, and the solubilized Notch protein can then be purified using a metal chelating column under conditions that allow tight binding of the protein.

Notch may be expressed in *E. coli* in a poly-His tagged form, using the following procedure. The DNA encoding Notch is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) Ion galE rpoHts(htpRts) clpP(laclq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea. 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally. the properly refolded species of most proteins are eluted at the lowest concentrations of acetonitrile since those species are the most compact with their hydrophobic interiors shielded from interaction with the reversed phase resin. Aggreoated species are usually eluted at higher acetonitrile concentrations. In addition to resolving misfolded forms of proteins from the desired form, the reversed phase step also removes endotoxin from the samples.

Fractions containing the desired folded Notch polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine™ (Pharmacia) resins equilibrated in the formulation buffer and sterile filtered.

Example 10
Expression of Notch in Mammalian Cells

This example illustrates preparation of a potentially glycosylated form of Notch by recombinant expression in mammalian cells.

The vector, pRK5 (see EP 307,247, published Mar. 15, 1989), is employed as the expression vector. Optionally, the Notch DNA is ligated into pRK5 with selected restriction enzymes to allow insertion of the Notch DNA using ligation methods such as described in Sambrook et al., supra. The resulting vector is called pRK5-Notch.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-Notch DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of Notch polypeptide. The cultures containing transfected cells may undergo further incubation (in serum free medium) and the medium is tested in selected bioassays.

In an alternative technique, Notch may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-Notch DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed Notch can then be concentrated and purified by any selected method, such as dialysis and/or column chromatography.

In another embodiment, Notch can be expressed in CHO cells. The pRK5-Notch can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of Notch polypeptide, the culture medium may be replaced with serum free medium. Preferably, the cultures are incubated for about 6 days, and then the conditioned medium is harvested. The medium containing the expressed Notch can then be concentrated and purified by any selected method.

Epitope-tagged Notch may also be expressed in host CHO cells. The Notch may be subcloned out of the pRK5 vector. The subclone insert can undergo PCR to fuse in frame with a selected epitope tag such as a poly-his tag into a Baculovirus expression vector. The poly-his tagged Notch insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged Notch can then be concentrated and purified by any selected method, such as by $Ni^{2+}$-chelate affinity chromatography.

Notch may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774–1779 (1996), and uses the SV40 early promoter/enhancer to drive expression of the CDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 μL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filler. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 MM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer. pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 11

Expression of Notch in Yeast

The following method describes recombinant expression of Notch in yeast.

First, yeast expression vectors are constructed for intracellular production or secretion of Notch from the ADH2/GAPDH promoter. DNA encoding Notch and the promoter is inserted into suitable restriction enzyme sites in the selected plasmid to direct intracellular expression of Notch. For secretion, DNA encoding Notch can be cloned into the selected plasmid, together with DNA encoding the ADH2/GAPDH promoter, a native Notch signal peptide or other mammalian signal peptide, or, for example, a yeast alpha-factor or invertase secretory signal/leader sequence, and linker sequences (if needed) for expression of Notch.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant Notch can subsequently be isolated and purified by removing the yeast cells from the fermentation medium by centrifugation and then concentrating the medium using selected cartridge filters. The concentrate containing Notch may further be purified using selected column chromatography resins.

Example 12

Expression of Notch in Baculovirus-Infected Insect Cells

The following method describes recombinant expression of Notch in Baculovirus-infected insect cells.

The sequence coding for Notch is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding Notch or the desired portion of the coding sequence of Notch such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged Notch can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes. pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 $\mu$m filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$ tagged Notch are pooled and dialyzed against loading buffer.

Alternatively, purification of the IgG tagged (or Fc tagged) Notch can be performed using known chromatography techniques, including for instance, Protein A or protein G column chromatography.

Example 13

Preparation of Antibodies that Bind Notch

This example illustrates preparation of monoclonal antibodies which can specifically bind Notch.

Techniques for producing the monoclonal antibodies are known in the art and are described, for instance, in Goding, supra. Immunogens that may be employed include purified Notch, fusion proteins containing Notch, and cells expressing recombinant Notch on the cell surface. Selection of the immunogen can be made by the skilled artisan without undue experimentation.

Mice, such as Balb/c, are immunized with the Notch immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-Notch antibodies.

After a suitable antibody titer has been detected, the animals "positive" for antibodies can be injected with a final intravenous injection of Notch. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against Notch. Determination of "positive" hybridoma cells secreting the desired monoclonal antibodies against Notch is within the skill in the art.

The positive hybridoma cells can be injected intraperitoneally into syngeneic Balb/c mice to produce ascites containing the anti-Notch monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 14

Purification of Notch Polypeptides Using Specific Antibodies

Native or recombinant Notch polypeptides may be purified by a variety of standard techniques in the art of protein purification. For example, pro-Notch polypeptide, mature Notch polypeptide, or pre-Notch polypeptide is purified by immunoaffinity chromatography using antibodies specific for the Notch polypeptide of interest. In general, an immunoaffinity column is constructed by covalently coupling the anti-Notch polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SFPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of Notch polypeptide by preparing a fraction from cells containing Notch polypeptide in a soluble form. This preparation is derived by solubilization of the whole cell or of a subcellular fraction obtained via differential centrifugation by the addition of detergent or by other methods well known in the art. Alternatively, soluble Notch polypeptide containing a signal sequence may be secreted in useful quantity into the medium in which the cells are grown.

A soluble Notch polypeptide-containing preparation is passed over the immunoaffinity column, and the column is washed under conditions that allow the preferential absorbance of Notch polypeptide (e.g., high ionic strength buffers in the presence of detergent). Then, the column is eluted under conditions that disrupt antibody/Notch polypeptide binding (e.g., a low pH buffer such as approximately pH 2–3, or a high concentration of a chaotrope such as urea or thiocyanate ion), and Notch polypeptide is collected.

Example 15

Drug Screening

This invention is particularly useful for screening compounds by using Notch polypeptides or binding fragment thereof in any of a variety of drug screening techniques. The Notch polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the Notch polypeptide or fragment. Drugs are screened against such transformed cells in competitive binding assays. Such cells, either in viable or fixed form, can be used for standard binding assays. One may measure, for example, the formation of complexes between Notch polypeptide or a fragment and the agent being tested. Alternatively, one can examine the diminution in complex formation between the Notch polypeptide and its target cell or target receptors caused by the agent being tested.

Thus, the present invention provides methods of screening for drugs or any other agents which can affect a Notch polypeptide-associated disease or disorder. These methods comprise contacting such an agent with a Notch polypeptide or fragment thereof and assaying (I) for the presence of a complex between the agent and the Notch polypeptide or fragment, or (ii) for the presence of a complex between the Notch polypeptide or fragment and the cell, by methods well known in the art. In such competitive binding assays, the Notch polypeptide or fragment is typically labeled. After suitable incubation, free Notch polypeptide or fragment is separated from that present in bound form, and the amount of free or uncomplexed label is a measure of the ability of the particular agent to bind to Notch polypeptide or to interfere with the Notch polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a Notch polypeptide, the peptide test compounds are reacted with Notch polypeptide and washed. Bound Notch polypeptide is detected by methods well known in the art. Purified Notch polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding Notch polypeptide specifically compete with a test compound for binding to Notch polypeptide or fragments thereof. In this manner, the antibodies can be used to detect the presence of any peptide which shares one or more antigenic determinants with Notch polypeptide.

Example 16

Rational Drug Design

The goal of rational drug design is to produce structural analogs of biologically active polypeptide of interest (i.e., a Notch polypeptide) or of small molecules with which they interact, e.g., agonists, antagonists, or inhibitors. Any of these examples can be used to fashion drugs which are more active or stable forms of the Notch polypeptide or which enhance or interfere with the function of the Notch polypeptide in vivo (cf., Hodgson, *Bio/Technology*, 9: 19–21 (1991)).

In one approach, the three-dimensional structure of the Notch polypeptide, or of a Notch polypeptide-inhibitor complex, is determined by x-ray crystallography, by computer modeling or, most typically, by a combination of the two approaches. Both tie shape and charges of the Notch polypeptide must be ascertained to elucidate the structure and to determine active site(s) of the molecule. Less often, useful information regarding the structure of the Notch polypeptide may be gained by modeling based on the structure of homologous proteins. In both cases, relevant structural information is used to design analogous Notch polypeptide-like molecules or to identify efficient inhibitors. Useful examples of rational drug design may include molecules which have improved activity or stability as shown by Braxton and Wells, *Biochemistry*, 31:7796–7801 (1992) or which act as inhibitors. agonists, or antagonists of native peptides as shown by Athauda et al., *J. Biochem.*, 113:742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention. sufficient amounts of the Notch polypeptide may be made available to perform such analytical studies as X-ray crystallography. In addition, knowledge of the Notch polypeptide amino acid sequence provided herein will provide guidance to those employing computer modeling techniques in place of or in addition to x-ray crystallography.

What is claimed is:

1. A method of decreasing the proliferation of prostatic epithelial cells in a mammal, comprising administering to said mammal, an effective amount of a Notch1 polypeptide or an agonist thereof.

2. A method of decreasing the proliferation of prostatic epithelial cells comprising contacting a Notch1 receptor, on said prostatic epithelial cells with a Notch1 receptor agonist, thereby activating said Notch1 receptor and decreasing the proliferation of said prostatic epithelial cells.

3. The method of claim 2, wherein the step of contacting occurs in vitro.

4. The method of claim 2, wherein said agonist is an anti-Notch1 polypeptide antibody.

5. The method of claim 2 wherein said agonist is an antibody fragment.

6. The method of claim 5 wherein the antibody fragment is a Fab fragment.

7. The method of claim 2, wherein said agonist is a soluble Notch1 polypeptide ligand.

8. The method of claim 7 wherein said soluble Notch1 polypeptide ligand is selected from the group consisting of Jagged1, Jagged2, Delta and Delta4.

9. The method of claim 2, wherein the prostatic epithelial cells are derived from a Notch1 receptor expressing cancer.

* * * * *

UNITED STATES PATENT AND TRADEMARK OFFICE
CERTIFICATE OF CORRECTION

PATENT NO.    : 6,689,744 B2
DATED         : February 10, 2004
INVENTOR(S)   : Gao et al.

It is certified that error appears in the above-identified patent and that said Letters Patent is hereby corrected as shown below:

Column 4,
Line 20, delete "agonist Proliferation" and insert therefor -- agonist. Proliferation --.

Column 9,
Line 43, delete "serum albuntin" and insert therefor -- serum albumin --.

Column 12,
Line 9, delete "myelorna" and insert therefor -- myeloma --.
Lines 28 and 33, delete "mycloma" and insert therefor -- myeloma --.
Line 33, delete "beteromyeloma" and insert herefor -- heteromyeloma --.

Column 14,
Line 31, delete "Le.," and insert therefor --i.e., --.

Column 15,
Line 43, delete "E. Col" and insert therefor -- E. Coli --.

Column 16,
Line 23, delete "WO98102463" and inser therefor -- WO98/02463 --.

Column 18,
Line 24, delete "transfeetion" and insert therefor -- transfection --.

Column 20,
Line 53, delete "gycol. polypropylene" and insert therefor -- glycol, polypropylene --.

Column 22,
Line 52, delete "y ethyl-L-glutamate" and insert therefor -- γ ethyl-L-glutamate --.

Column 23,
Line 60, delete "wilt" and insert therefor -- will --.

Column 25,
Line 22, delete "Notchi" and inseret terefor -- Notch1 --.

Column 27,
Line 54, delete "AU " and insert therefor -- All --.

Column 28,
Line 48, delete "Jageed1" and insert therefor -- Jagged1 --.
Line 57, delete "Jageed2" and insert therefor -- Jagged2 --.

UNITED STATES PATENT AND TRADEMARK OFFICE
CERTIFICATE OF CORRECTION

PATENT NO. : 6,689,744 B2
DATED : February 10, 2004
INVENTOR(S) : Gao et al.

It is certified that error appears in the above-identified patent and that said Letters Patent is hereby corrected as shown below:

<u>Column 30,</u>
Line 4, delete "Notziger" and insert therefor -- Nofziger --.
Line 11, delete "Fort-eight" and insert therefor -- Forty-eight --.

<u>Column 31,</u>
Line 58, delete "Aggreoated" and insert therefor -- Aggregated --.

<u>Column 38,</u>
Line 33, delete "tie" and insert therefor -- the --.

Signed and Sealed this

Sixth Day of July, 2004

JON W. DUDAS
*Acting Director of the United States Patent and Trademark Office*